(12) United States Patent
Zeng et al.

(10) Patent No.: US 11,504,046 B2
(45) Date of Patent: Nov. 22, 2022

(54) GRAPH TOTAL VARIATION FOR ECGI

(71) Applicants:CARDIOINSIGHT TECHNOLOGIES, INC., Independence, OH (US); CASE WESTERN RESERVE UNIVERSITY, Cleveland, OH (US)

(72) Inventors: Qingguo Zeng, Solon, OH (US); Richard N. Lartey, Independence, OH (US); Weihong Guo, Solon, OH (US)

(73) Assignees: CARDIOINSIGHT TECHNOLOGIES, INC., Independence, OH (US); CASE WESTERN RESERVE UNIVERSITY, Cleveland, OH (US)

( * ) Notice: Subject to any disclaimer, the term of this patent is extended or adjusted under 35 U.S.C. 154(b) by 439 days.

(21) Appl. No.: 16/688,286

(22) Filed: Nov. 19, 2019

(65) Prior Publication Data

US 2020/0155022 A1 May 21, 2020

Related U.S. Application Data

(60) Provisional application No. 62/769,320, filed on Nov. 19, 2018.

(51) Int. Cl.
*A61B 5/339* (2021.01)
*A61B 5/00* (2006.01)
(Continued)

(52) U.S. Cl.
CPC ............ *A61B 5/339* (2021.01); *A61B 5/6801* (2013.01); *G06F 17/11* (2013.01); *G06T 17/20* (2013.01); *G06T 19/00* (2013.01)

(58) Field of Classification Search
CPC ....... A61B 5/6801; G06F 17/11; G06T 17/20; G06T 19/00
See application file for complete search history.

(56) References Cited

U.S. PATENT DOCUMENTS

| 7,505,810 B2 * | 3/2009 | Harlev | A61B 5/287 |
| | | | 600/509 |
| 2007/0299352 A1 * | 12/2007 | Harlev | A61B 5/6852 |
| | | | 600/509 |

(Continued)

OTHER PUBLICATIONS

Sen Yang, et al., "An Efficient ADMM Algorithm for Multidimensional Anisotropic Total Variation Regularization Problems"; Publication, Center for Evolutionary Medicine and Informatics, The Biodesign Institute; Aug. 13, 2013; 9 pgs.

(Continued)

*Primary Examiner* — Abderrahim Merouan
(74) *Attorney, Agent, or Firm* — Tarolli, Sundheim, Covell & Tummino LLP

(57) ABSTRACT

Systems and methods for graph total variation (GTV) based reconstruction of electrical potentials on a cardiac surface are disclosed. GTV-based systems and methods incorporate information about the graph structure of the heart surface as well as imposing sparsity constraints on neighboring nodes. To this end, the present disclosure uses a novel way of calculating derivatives on irregular meshes, and provides a fast solver to compute an inverse solution more efficiently than in previous systems and methods. Moreover, fast-changing signals can be recovered with less smoothing and thus greater fidelity to the original signals.

20 Claims, 6 Drawing Sheets

(51) Int. Cl.
  *G06F 17/11*    (2006.01)
  *G06T 17/20*    (2006.01)
  *G06T 19/00*    (2011.01)

(56) References Cited

U.S. PATENT DOCUMENTS

2009/0281439 A1* 11/2009 Harlev .................. A61B 5/339
                                                   600/509
2012/0184858 A1*  7/2012 Harlev .................. A61B 5/283
                                                   600/509
2019/0336023 A1* 11/2019 Lou ..................... A61B 5/361
2020/0163570 A1*  5/2020 Lou ..................... A61B 5/7275

OTHER PUBLICATIONS

Jingjia Xu, et al., "Noninvasive Transmural Electrophysiological Imaging Based on Minimization of Total-Variation Functional" IEEE Transactions on Medical Imaging, vol. 33, No. 9, Sep. 2014, 15 pgs.

Ying Li, et al., "Graph Fractional-Order Total Variation EEG Source Reconstruction"; Published in: 2016 38th Annual International Conference of the IEEE Engineering in Medicine and Biology Society (EMBC); Aug. 16-20, 2016; 4 pgs.

Huahua Wang, et al., "Bregman Alternating Direction Method of Multipliers"; Publication—Advances in Neural Information Processing Systems, Jan. 4, 2014, 2816-2824.

* cited by examiner

GRAPH TOTAL VARIATION FOR ECGI

CROSS-REFERENCE TO RELATED APPLICATION

This application claims the benefit of U.S. Provisional Patent Application 62/769,320 filed on 19 Nov. 2018, and entitled GRAPH TOTAL VARIATION FOR ECGI, the entirety of which is incorporated herein by reference.

TECHNICAL FIELD

This disclosure relates to detection and analysis of cardiac waveforms, and particularly to systems and methods using graph total variation (GTV).

BACKGROUND

An electrocardiogram (ECG) system monitors electrical activity of a heart of a patient via invasive or external electrodes. An electrophysiology (EP) procedure uses single or multiple catheters within the heart to assess the electrical activity and conduction pathways of the heart.

What is known as the "inverse problem" can be solved to reconstruct electrical activity inside a body surface based on measured electrical activity on the body surface. One example of such an application relates to electrocardiographic imaging (ECGI) wherein electrical potentials measured on a torso can be combined with geometry information to reconstruct electrical potentials on a cardiac surface. For example, a computer can combine and process the body surface electrical potentials activity data and the geometry data to reconstruct estimates of the cardiac surface potentials (e.g., epicardial potentials).

SUMMARY

As one example, a graph total variation (GTV) based electrogram reconstruction method is provided. Based on geometry data indicative of geometrical properties of body and cardiac surfaces, a transfer matrix is constructed that relates acquired cardiac electrical data, representing electrophysiological signals collected via a plurality of body surface measurement channels, to a plurality of cardiac surface node coefficients. For each of a plurality of target nodes among cardiac surface nodes in the geometry data, up to a predetermined maximum number of reference nodes are selected from among the cardiac surface nodes neighboring the target node, the distances between the target node and each reference node are calculated, and elements of a set of differential operator matrices are normalized based on the calculated distances to provide normalized differential operator matrices. Then, an alternating direction method of multipliers (ADMM) is used to iteratively compute reconstructed cardiac surface potentials based on the collected cardiac electrical data, the transfer matrix, and the normalized differential operator matrices.

As another example, a system includes non-transitory memory to store electrical data representing a plurality of ECG signals, geometry data and machine-readable instructions and a processor to access the non-transitory memory and execute the machine-readable instructions. The instructions include a transfer matrix generator programmed to construct a transfer matrix that relates collected electrophysiological data from a plurality of body surface measurement channels to a plurality of cardiac surface node coefficients, based on geometry data representing spatial geometry of the body surface and spatial geometry of a cardiac surface in a three-dimensional coordinate system. The instructions further include a spatial derivative operator calculator programmed to calculate a set of spatial derivative operators based on the cardiac surface geometry data. The instructions further include a graph total variation (GTV) optimizer programmed to iteratively compute, using an (ADMM), reconstructed cardiac surface potentials based on the collected electrophysiological data, the transfer matrix, and the spatial derivative operators.

As yet another example, a system includes an array of electrophysiological sensors configured to be placed on a body surface of a patient and thereby to produce electrical measurement data corresponding to electrical potentials measured from the body surface, and a mapping system that includes an electrogram reconstruction engine. The electrogram reconstruction engine is configured to reconstruct electrograms on a cardiac surface based on the electrical measurement data and on geometry data, the geometry data representing spatial geometry of the body surface and the cardiac surface in a three-dimensional coordinate system. The electrogram reconstruction engine uses a graph total variation (GTV) regularization that normalizes the elements of a set of differential operator matrices based on calculated distances between target and neighboring reference nodes in the cardiac surface geometry data and iteratively computes, by an alternating direction method of multipliers (ADMM), reconstructed cardiac surface potentials based on the electrical measurement data and the differential operator matrices. A display is configured to visualize a graphical map that is based on the reconstructed electrograms.

DETAILED DESCRIPTION

Figure 1:
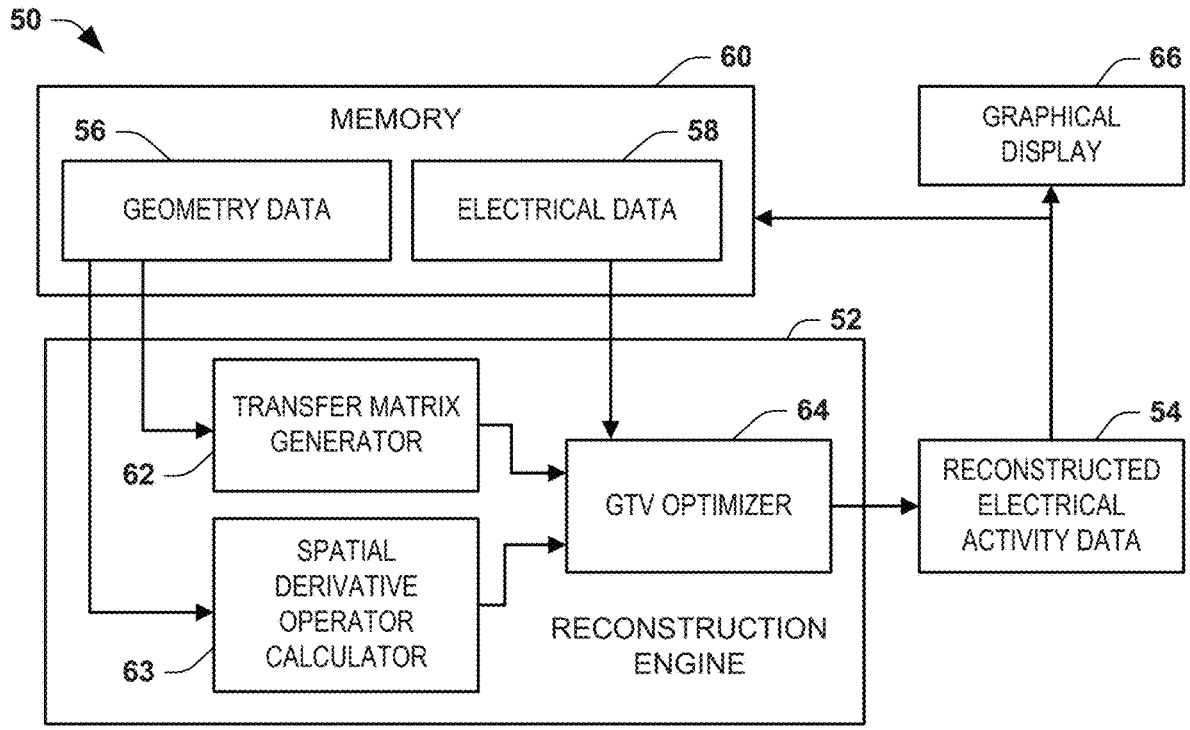
FIG. 1 is a block diagram of an example system to reconstruct electrical activity on a cardiac surface from measured body surface potentials using graph total variation (GTV) regularization in the reconstruction.

This application discloses systems and methods for graph total variation (GTV) regularization for examining measured body surface potentials (BSP) in the framework of noninvasive electrocardiography (ECG), particularly to improve inverse problem solutions for electrophysiology.

As used herein, an "electrocardiogram signal" ("ECG signal") refers to a graph of voltage over time recorded for one or more channels each based on a cardiac electrical signal sensed by an electrode. ECG signals can be generated from body surface measurements. In some examples, the ECG signals can be used to reconstruct electrograms on a cardiac envelope that are computed by solving an inverse problem based on electrical signals acquired from a set of non-invasive body surface measurements and geometry data that relates the body surface measurement locations with respect to the cardiac envelope. When computing reconstructed cardiac-surface electrograms from body surface measurements (BSMs), current approaches involving the method of fundamental solutions (MFS) or the boundary element method (BEM) result in reconstructed signals that are smeared or smoothed in such a way that sharp spatial detail in the electrophysiological signals is lost. For example, the current MFS approach cannot recover a very sharp R wave in reconstructed electrograms. In particular, reconstruction techniques based on Tikhonov regularization, such as the minimum norm estimates (MNE) and low resolution electrical tomography (LORETA), use the $l^2$-norm, which results in relatively low spatial resolutions of the reconstructed inverse and thereby promotes undesirable smoothing of spatial signal detail. Total variation (TV) based methods improve the sharpness of edges of the reconstructed sources, but fail to account for the complex structure of the underlying surface triangulations. Systems and methods disclosed herein employ a graph total variation (GTV) based scheme to incorporate information about the graph structure of the heart surface as well as imposing sparsity constraints on neighboring nodes. To this end, the present disclosure uses GTV on ECGI, involves a novel way of calculating derivatives on irregular meshes, and provides a fast solver to compute an inverse solution more efficiently than in previous systems and methods. Moreover, sharper R waves can be recovered with less smoothing that are more truthful to the original signals.

The presently disclosed systems and methods can make reconstructed electrograms more specific by reducing smoothing effects in the solver, yielding improvements to ECGI reconstruction accuracy and thereby providing a breakthrough in ECGI technology compared to existing approaches. The GTV ECG-potential reconstruction systems and methods disclosed herein are based on TV and improve the reconstruction accuracy of reconstructed cardiac surface potentials. Specifically, the described GTV systems and methods extend TV, which is defined on a two-dimensional rectangular grid, to an irregular three-dimensional surface of triangulations. Using the graph of the triangulated surface, a differential operator can be defined for the spatial derivatives at each source localization. In contrast to other reconstruction accuracy improvement attempts that have explored the graph structure of the source surface, in some examples of the presently disclosed systems and methods, only neighboring source nodes that are one layer away from a particular node (k=1) are considered when normalizing differential operator matrices. The disclosed systems and methods can use an iterative scheme to find optimal estimates to the inverse problem, which scheme can be derived using the split Bregman (SB) method or other proximal algorithms, such as a forward-backward splitting algorithm or a primal-dual algorithm, to recover the source potentials. In other examples, other approaches may be used to select nodes for inclusion in normalizing differential operator matrices, such as setting a threshold distance (e.g., radius) from a target node. In such examples, all neighbor nodes within a predefined target-reference threshold distance (e.g., one-half centimeter, or one centimeter, or two centimeters) can be selected as reference nodes.

The GTV-based systems and methods described herein are generalized in terms of the form of the reconstruction surface graph. Using GTV, the numerical computations from one node to the other are more localized and can be used to compute the differences in terms of how sharp are the changes from one node to another. The GTV approaches described herein can operate on small local spatial neighborhoods of reconstruction surface nodes wherein such nodes are not necessarily equidistant, in a fairly large domain.

As compared to existing state-of-the-art techniques, the systems and methods disclosed herein provide superior performance with regards to spatial resolution and localization accuracy, thus permitting more accurate diagnosis of cardiac defects or disease and more accurate targeting of therapies such as ablation or drug delivery. Reconstructed cardiac surface potentials can be used, for example, to generate one or more graphical visualizations to present spatially and temporally consistent information in one or more cardiac maps. The visualized spatial location of identified signal source points on the cardiac anatomy can be used for diagnosis as well as a clinical target for performing a therapy.

As used herein, the terms "cardiac surface" and "cardiac envelope" can correspond to an epicardial surface of a patient's heart, an epicardial surface of model heart (the patient's or a generic heart) or to any surface boundary within the patient's body having a known spatial relationship with respect to the patient's heart or a model heart.

FIG. 1 demonstrates an example system 50 to reconstruct electrograms (i.e., time-variant electrical potentials) on a cardiac envelope, using GTV as part of the inverse solution. The system 50 includes reconstruction engine 52. The reconstruction engine 52 can generate reconstructed electrical activity data 54 by combining geometry data 56 and non-invasively measured electrical data 58, which can be stored in memory 60. Memory 60 can also store machine-readable instructions corresponding to the reconstruction engine 52.

In order to function to map body surface electrical data via inverse reconstruction to a cardiac envelope different from where the sensing has occurred, system 50 can use geometry data 56, which can include acquired sensing node geometry data for the sensing nodes. The acquired sensing node geometry data can identify the location of the sensing nodes (corresponding to sensing electrodes) in a respective spatially correlated system. For example, the sensing node geometry data can include a list of sensing nodes, and neighbors for each sensing node, and spatial coordinates of each node. The nodes and spatial coordinates can be produced by segmenting imaging data that has been acquired by an appropriate imaging modality or other non-imaging methods. Examples of imaging modalities include ultrasound, computed tomography (CT), three-dimensional rotational angiography (3DRA), magnetic resonance imaging (MRI), X ray, positron emission tomography (PET), fluoroscopy, and the like. Such imaging can be performed separately, i.e., before or after the measurements utilized to generate the electrical data 58, or, alternatively, such imaging may be performed concurrently with recording the electrical activity that is utilized to generate the electrical data 58. In other examples, the sensing node geometry data can also be acquired by manual measurements between sensing nodes or other means (e.g., a laser digitizer).

The sensing node geometry data in geometry data 56 can thus include coordinates (e.g., in three-dimensional space) for each of the sensing nodes. Distances between such sensing nodes can be computed for neighboring sensing nodes based on the coordinates (e.g., according to a distance metric, such as Euclidean distance or geodesic distance). These sensing node distances can be stored in memory 60 as part of geometry data 56 or can be computed from the sensing node coordinates by the system 50 without storage in memory 60.

In addition to sensing node geometry data, geometry data 56 can include anatomical surface geometry data that geometrically defines the anatomical surface of an anatomical structure, such as the heart, either from a predefined three-dimensional model of an anatomical surface or from a model computed or derived from data acquired via an imaging modality like one of those listed above. The geometry data 56 thus can include both torso and anatomical structure (e.g., heart) surface node coordinates (e.g., in three-dimensional space) and corresponding connectivity lists for nodes across each surface.

The electrical data 58 can include torso surface potentials measured over time by electrophysiological sensors (e.g., ECG electrodes) placed at the aforementioned torso coordinates. The reconstruction engine 52 can be configured or programmed to include a transformation matrix generator 62, spatial derivative operator calculator 63, and GTV optimizer 64, which can implement an iterative method as disclosed herein. The spatial derivative operator calculator 63 can include a function to decide on the number of spatial derivatives and nearest neighbors over which the spatial derivatives should be computed, as described herein. The functions of reconstruction engine 52 can be performed, for example, by one or more computer processors in communication with memory 60.

In some examples, a disconnected channel detector can operate on the body surface electrical data 58 to determine if any channels have been disconnected or are too noisy or of too high impedance to provide valid electrical data. As an example, the disconnected channel detector can be configured to detect saturation of an input channel such as by monitoring the value of the electrical signal. If the value of the electrical signal for a channel exceeds a threshold value (e.g., about ±500 mV) or has a predetermined value (e.g., 0 V) for a plurality of consecutive samples, the disconnected channel detector can determined the corresponding channel to be disconnected. As an example, a measurement system (e.g., measurement system 718 of FIG. 7) to which the input channel signals are provided can be configured to saturate and obtain a predetermined value (e.g., about ±500 mV) for a given channel if it loses contact with the body surface. In this way, the disconnected channel detector can determine a saturated or disconnected channel which will be removed from further processing, e.g., by removing the associated electrophysiological data from inclusion in electrical data 58 or marking such data to be ignored from processing.

The system in FIG. 1 thus includes a non-transitory memory 60 to store electrical data 58 representing a plurality of electrocardiogram signals, geometry data 56, and machine-readable instructions for electrogram reconstruction, and a processor (not shown) to access the non-transitory memory 60 and execute the machine-readable instructions. The instructions can include a reconstruction engine 52 that can include a transfer matrix generator 62 programmed to construct a transfer matrix that relates collected electrophysiological data from a plurality of body surface measurement channels to a plurality of cardiac surface node coefficients, based on geometry data representing spatial geometry of the body surface and spatial geometry of a cardiac surface in a three-dimensional coordinate system. The reconstruction engine 52 can further include a spatial derivative operator calculator 63 programmed to calculate a set of spatial derivative operators based on a portion of the cardiac surface geometry. The reconstruction engine 52 can further include a graph total variation (GTV) optimizer 64 programmed to iteratively compute, using an alternating direction method of multipliers (ADMM), reconstructed cardiac surface potentials based on the collected electrophysiological data, the transfer matrix, and the spatial derivative operators. Proximal algorithms other than ADMM, such as a forward-backward splitting algorithm or a primal-dual algorithm, can also be used to recover the source potentials. The split-Bregman ADMM approach has the advantages of simplicity and easy implementation, but under certain criteria, other methods can be equivalent and provide comparable results.

A system in accordance with FIG. 1 may also include an array of electrophysiological sensors (not shown) configured to be placed on a body surface of a patient and thereby to produce the electrical measurement data 58 corresponding to electrical potentials measured from the body surface. The electrogram reconstruction engine 52 may be part of a mapping system. The GTV optimizer can implement a GTV regularization that normalizes the elements of a set of differential operator matrices based on calculated distances between target and neighboring reference nodes on the cardiac surface and iteratively computes, by ADMM, reconstructed cardiac surface potentials based on the electrical measurement data and the differential operator matrices. The system of FIG. 1 can further include a display 66 configured to visualize a graphical map that is based on the reconstructed electrograms.

Figure 2:
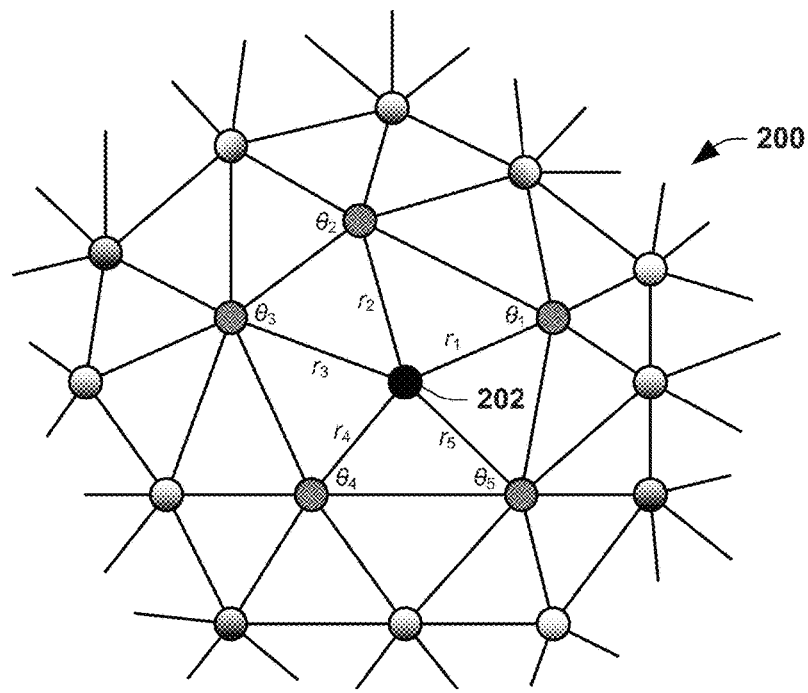
FIG. 2 is an example portion of a graph of nodes.

FIG. 2 depicts a portion or subset of nodes 200 in the form of a mesh of nodes distributed across a geometric surface. The subset of nodes 200 can correspond to a portion of a body surface mesh or another anatomical surface mesh, such as a heart surface mesh. In the case of a body surface mesh, for example, each node represents the position of an electrophysiological sensor placed on the body surface. Solving the ECG inverse problem involves reconstructing cardiac surface potentials, electrograms, recovery sequences and regions of equivalent activation times (isochrones) using source localizations on the body surface. For example, an inverse problem using M body surface nodes representing the source electrocardiograms measured on the torso surface that has been discretized into P triangles, where M and P are positive integers.

FIG. 2 thus can depict a layered diagram of nodes 200 demonstrating an example of a neighborhood for a given target node 202 on a cardiac surface onto which electrograms are to be reconstructed. A subset of the nodes surrounding a target node 202 can define the given node's neighboring nodes. The neighboring nodes of the target node can include an arrangement of nodes having a plurality of layers that provide a multi-layer neighborhood of the nodes for the target node (e.g., the vertex) 202. Each respective layer k around the target node can be defined based on spatial connectivity and/or spatial distance with respect to the given node. For example, a first layer of neighboring nodes can surround (e.g., circumscribe) just the given node 202. "Neighborhood" here is given the traditional definition in graph theory, except that the neighborhood can be considered to be limited in all cases to k=5 layers. In some examples, as few as k=1 layer of neighbor nodes are considered for each target node. In other examples, a neighborhood for a given target node may be defined in terms of a distance (e.g., Euclidean or other distance) from the given target node.

In the illustrated example of FIG. 2, node 202 has five immediate neighbors in the first layer away from node 202 (k=1), which are shaded in FIG. 2, but a target node can have more or fewer such first-layer neighbor nodes depending on the topology of the mesh 200. In FIG. 2, the nodes in the first layer can correspond to search directions $\theta_1$, $\theta_2$, $\theta_3$, $\theta_4$, and $\theta_5$, which are angles relative to the target node. The reference nodes in the first layer are each a respective three-dimensional distance $r_1$, $r_2$, $r_3$, $r_4$, and $r_5$ away from target node 202 along a respective virtual line at the respective search direction $\theta_1$, $\theta_2$, $\theta_3$, $\theta_4$, or $\theta_5$. Such a distance can be computed as either a Euclidean distance or a geodesic distance from the target node 202 to the corresponding reference node. A second layer of the neighborhood 200 (k=2) can include another subset of nodes that surround the first layer and the given node. The nodes in such second layer are represented as unshaded vertices in FIG. 2. Neighborhood 200 can include additional layers (k>2) (not illustrated). As an example, neighbors of a target node 202 can be examined as reference nodes one by one, each reference node and target node having a difference vector therebetween, the difference vector having an angle θ (with respect to an x axis) and a distance r. For purposes of computational efficiency, the methods and systems herein can confine the neighbor search for reference nodes to a predefined number L of layers, e.g., one layer, and a predefined number Θ of search directions, e.g., eight, as viewed from the target node.

In the following examples, $b_t \in \mathbb{R}^M$ denotes body surface measurements b made at time instance t. Just as a body surface can be discretized into M body surface nodes forming P triangles, a cardiac surface can be discretized into N cardiac surface nodes forming K triangles, and information representing the locations of and edges connecting these surface nodes can be stored in memory 60 as part of geometry data 56. Provided the data inputs 56, 58, reconstruction engine 52 can function according to the below description to estimate the cardiac surface potentials u on a cardiac surface $u_t \in \mathbb{R}^N$ such that $$b_t = Au_t + \varepsilon_t \quad (1)$$

where $\varepsilon_t \in \mathbb{R}^M$ denotes noise, and $A \in \mathbb{R}^{M \times N}$ is the transfer matrix, a linear operator constructed based on geometrical properties of both the torso and cardiac surfaces. In general A is rectangular, since M<<N, corresponding to the ill-posed nature of the inverse problem. To promote the uniqueness of the solution, the presently described systems and methods utilize a fitting regularization technique with sparsity constraints on the spatial derivatives.

Figure 3:
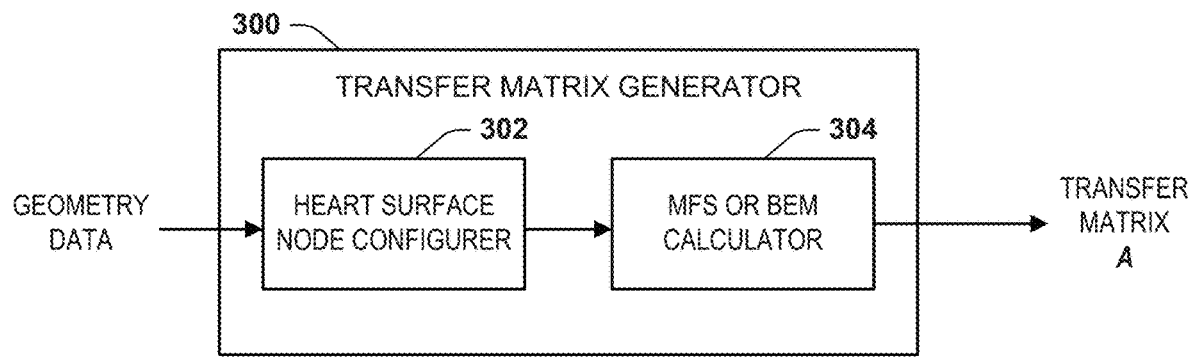
FIG. 3 is a block diagram of an example transfer matrix generator.

FIG. 3 illustrates an example transfer matrix generator 300 that can correspond to transfer matrix generator 62 in FIG. 1. In some examples, transfer matrix generator 300 can include virtual node configurer 302. Transfer matrix generator 300 can also include a calculator 304 programmed to compute a transfer matrix A, such as according to one of the method of fundamental solutions (MFS) or boundary element method (BEM). In examples having virtual node configurer 302, such as examples wherein calculator 304 computes transfer matrix A by MFS, virtual node configurer 302 can configure virtual nodes placed to define two surfaces of arbitrary shape, one that is outside the torso surface and one that is inside the heart surface. The virtual nodes can be configured according to either of two approaches: a static configuration where the virtual nodes that define the fictitious boundaries are placed at fixed and pre-selected locations, or a dynamic configuration where the locations of the virtual nodes are determined dynamically by a nonlinear optimization procedure.

In an example static configuration, a set of outer surface virtual nodes are placed at locations spaced from the torso surface (e.g., parallel to and spaced some distance outward therefrom) and a set of inner surface virtual nodes are placed at locations spaced from the cardiac surface (e.g., parallel to and spaced some distance inward therefrom). The virtual nodes can be defined such that the outer surface virtual nodes are placed some fixed distance outward from each torso node along the rays extending from a central point representing the geometric center of the heart through each of the torso nodes, and the inner surface virtual nodes are placed some fixed distance inward from each cardiac surface node along the rays extending from the central point through each of the cardiac surface nodes. The geometric center of the heart can be determined by segmentation. As an example, a ratio of 1.2:1 can be used for configuring virtual nodes from the torso nodes and a ratio of 0.8:1 can be used for configuring virtual nodes for the cardiac surface nodes. Other ratios may be used in other examples. In this example (wherein each virtual node that defines the fictitious surface outside the torso surface is inflated at a 1.2:1 ratio), if a given torso node is located 1 unit of measurement from the central point, then the virtual node corresponding to that torso node would be located along a ray extending from the central point through that torso node at a location 1.2 units of measurement from the central point. Also with this example (wherein each virtual node that defines the fictitious surface inside the cardiac surface is deflated at a 0.8:1 ratio), if a given cardiac surface node is located 1 unit of measurement from the central point, then the virtual node corresponding to that cardiac surface node would be located along a ray extending from the central point through that cardiac surface node at a location 0.8 units of measurement from the central point.

MFS or BEM calculator 304 can calculate transfer matrix A that translates measured torso potentials at each torso node to a plurality of heart surface node coefficients based on the input geometry data using either MFS or BEM methods. An example MFS method is described in U.S. Pat. No. 7,983,743 B2 to Rudy et al. An example BEM method is discussed in U.S. Pat. No. 6,772,004 B2 to Rudy et al. Both of these disclosures are incorporated by reference.

Figure 4:
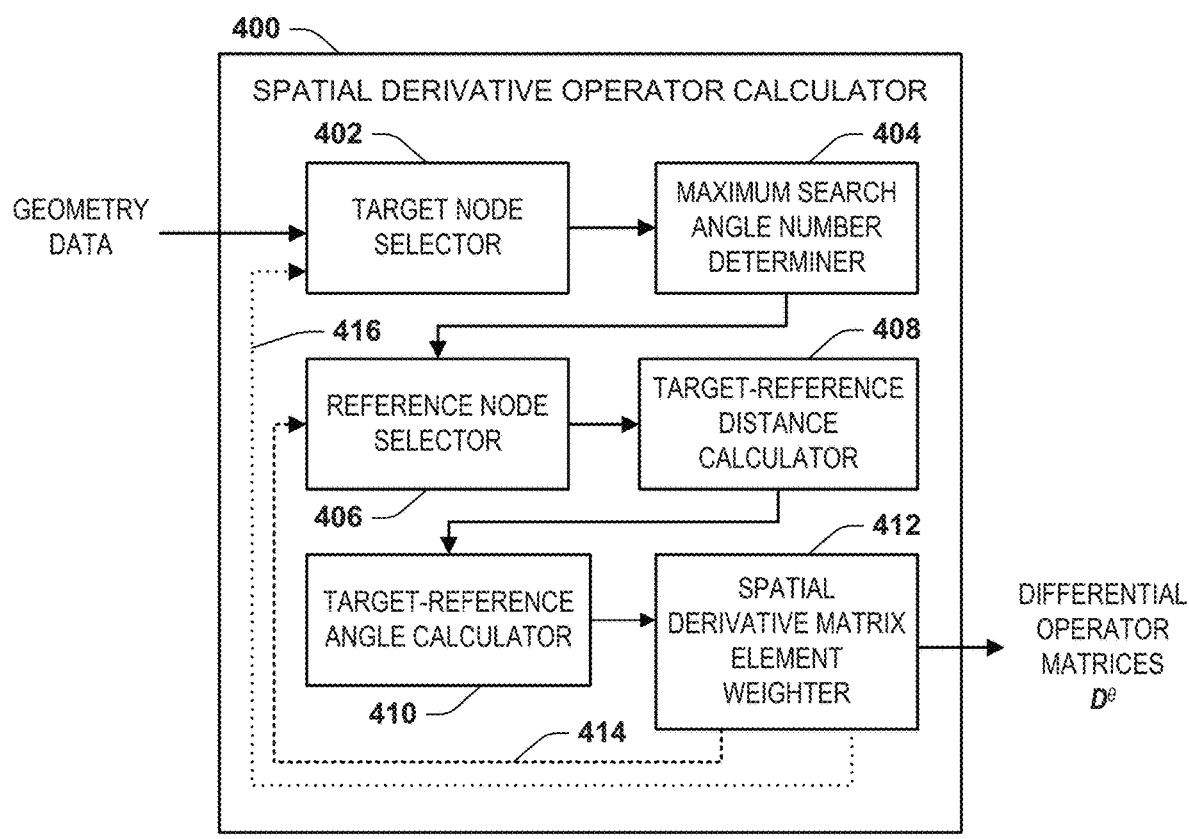
FIG. 4 is a block diagram of an example spatial derivative operator calculator.

FIG. 4 illustrates an example spatial derivative operator calculator 400 that can correspond to spatial derivative operator calculator 63 in FIG. 1. Spatial derivative operator calculator 400 can include target node selector 402, maximum search angle number determiner 404, reference node selector 406, target-reference distance calculator 408, target-reference angle calculator 410, and spatial derivative operator matrix element weighter 412, to produce output differential operator matrices $D^\theta$ from input geometry data, such as may be included in geometry data 56 in FIG. 1, representative of the three-dimensional spatial positions of and connectivity relationships between multiple nodes in a graph representative of a cardiac surface. Target node selector 402 selects a target node from amongst the multiple nodes in the heart surface graph or portion thereof. In some examples, the selection can be made by iterating through the list of heart surface nodes in the input geometry data or some subset thereof. In other examples, the selection can be made by sampling a portion of heart surface nodes in the geometry data until some density criterion is met, i.e., until a sufficient number of nodes have been analyzed. The density criterion can be a user-selectable parameter or can be a parameter that is dynamically or adaptively chosen by the reconstruction engine 52.

Maximum search angle determiner 404 can determine maximum number Θ of reference node search directions θ such that only a limited number of reference nodes are analyzed for each target node. This maximum number can be a user-configurable value or can be an adaptive value determined by reconstruction engine 52 based on the complexity of the heart surface mesh. As an example, maximum search angle number determiner 404 can set Θ to be about eight, e.g., five, six, seven, or eight. Maximum search angle determiner 404 determines a maximum number of search angles, not a maximum angle value in degrees.

Provided the maximum number of search angles for the selected target node being analyzed has not already been exhausted, reference node selector 406 can select a reference node that is a neighbor of the target node selected by target node selector 402, from amongst the nodes in the heart surface graph as defined by the input geometry data. Reference node selector 404 can be configured to select, for example, only first-layer neighbors (k=1) or only neighbors within a specified maximum number of layers. This search layer maximum parameter can be a user-selectable parameter or can be a parameter that is dynamically or adaptively chosen by the reconstruction engine 52. In the event that a target node has more first-layer neighbor nodes than the maximum number Θ of directions searched, then, as one example, a random selection of Θ first-layer neighbor nodes can be chosen as reference nodes, or, as another example, the Θ nearest neighbors can be selected as the reference nodes. As examples, the area around a target node can be separated into Θ equal sectors and one reference node can be chosen from each sector, either randomly or by some either criterion, such as choosing the neighbor node closest to the target node or choosing the neighbor node closest to the clockwise (or, alternatively, counter-clockwise) sector edge. A "sector" as used herein is defined by two coplanar rays emanating from the target node. Together, the target node selector 402 and the reference node selector 406 define a pair of nodes residing in a sector (i.e., the target node and a chosen reference node for that sector). Reference node selector 404 can also be configured to select, for example, all neighbors within a target-reference threshold distance, such as one-half centimeter, one centimeter, or two centimeters. In any of these neighbor-node selection examples, the graph around the reference node, i.e., the reference node and its neighbors that may be candidates for selection, can be considered as "flattened" into a two-dimensional graph, even though the graph may be a three-dimensional graph, e.g., by projecting the three-dimensional graph onto a two-dimensional plane, or by considering the search distance as a distance around the curve of the graph.

For a particular target-node/reference-node pair, target-reference distance calculator 408 can calculate a distance r between the two nodes in the heart surface graph. This distance r can be calculated as either a Euclidean distance or a geodesic distance. Similarly, target-reference angle calculator 410 can calculate an angle between the vector connecting the target and reference nodes and the x axis. Together this distance r and angle θ define this target-reference vector. The distance r can be computed as a three-dimensional difference despite the fact that the target node may have been selected by effectively "flattening" the graph, as described above, and the target-reference vector can be a three-dimensional vector. Spatial derivative matrix element weighter 412 can then weight the elements of a D matrix for the particular search angle θ taking into account the distance r. For each D matrix, each row corresponds to a relationship with a particular node. The number of non-zero rows indicates a number of nearest neighbors in each particular direction. Because the graph is a three-dimensional surface, weighter 412 can normalize each row by the three-dimensional geometric distance along the surface between two nodes in question. This distance is not necessarily a straight-line distance but can follow the curvature of the graph.

Spatial derivative operator calculator 400 can thus generate differential operator matrices based on the connectivity properties of the heart surface graph, which can be irregular, with nodes separated from each other by nonuniform distances. The differential operator matrices produced by spatial derivative operator calculator 400 thus take into account these distances by dividing unitary terms in a first-order spatial derivative D by these generally variable distances. As one example, spatial derivative operator calculator 400 can compute spatial derivative operator matrices Dθ, i.e., a separate D matrix for each neighbor search angle θ, that are modified from the N×N size D matrix used in the definition of the one-dimensional $l^1$-norm total variation (TV) operator $$TV(u) = \|\nabla u\|_1 = \|Du\|_1 = \sum_{i=1}^{N} |(Du)_i|, \quad (2)$$

where $D \in \mathbb{R}^{N \times N}$ approximates the spatial derivative. In the above TV operator definition, the first-order spatial derivative D can be defined as $$D = \begin{bmatrix} 1 & & & & \\ -1 & 1 & & & \\ & \ddots & \ddots & & \\ & & -1 & 1 & \\ & & & -1 & 1 \end{bmatrix}. \quad (3)$$

In the two-dimensional anisotropic TV operator, $$TV(u) = \|\nabla u\|_1 = \sum_{i,j=1}^{N} \left( |(D_x u)_{i,j}| + |(D_y u)_{i,j}| \right), \quad (4)$$

where $D_x/D_y$ represents the spatial derivative of cardiac surface potentials u along the x/y direction. Varying orders of smoothness can be achieved, for example, by using fractional derivatives based on the Grüwald-Letnikov derivative definition.

Due to the irregular three-dimensional surface of triangulations, such as illustrated in FIG. 2, spatial derivative operator calculator 400 can compute operators that can be used to find the spatial derivatives on the graph of heart surface nodes according to a spatial derivative operator definition modified from that given above. For a given target node among the plurality of nodes in the reconstructed heart surface graph, spatial derivative operator calculator 400 can be programmed to determine, with regards to a geodesic of the underlying surface, a set of reference nodes from among neighbors on the surface, and can iterate over the determined set of reference nodes as indicated by connection 414 in FIG. 4. Spatial derivative operator calculator 400 can also iterate over a set of target nodes as indicated by connection 416 in FIG. 4. As an example, for a specific target node vi, selected by target node selector 402, all paths with length of k=1 (i.e., to first-layer neighbor reference nodes) can be found starting from the ith node. Other examples can use other path lengths, e.g., k=2, k=3, but with potential cost of increased computational complexity.

The number of directions around the considered target node vi with reference to the x axis can be limited to a predetermined maximum number Θ of directions, as can be determined by maximum search angle number determiner 404. As examples, Θ can be equal to five or more, such as five, six, seven, or eight (or more). Thus, for example, spatial derivative operator calculator 400 may consider at most eight directions around each node vi. Other maximum numbers of reference nodes may be selected in other examples. In each search direction θ, nodes that have shortest distance k=1 away from $v_i$ (i.e., nearest neighbors to $v_i$) can be assigned weight −1 and node $v_i$ itself can be assigned weight 1. To account for the fact that the path lengths between target and reference nodes are not equal for each reference node around a target node, these assigned weights can be divided by the distance $r(v_i, v_θ)$ for each pair of nodes considered, as can be determined by target-reference distance calculator 408. For example, a Euclidean distance or a geodesic distance can be used for each distance r. In these ways, sparsity and the structure of the graph are enforced in the reconstruction. For each pair of reference and target nodes, target-reference angle calculator 410 can compute the angle θ between the x axis and the difference vector connecting the target node to the reference node.

The reconstruction engine 52 of FIG. 1 can use the following GTV regularization model for reconstruction of cardiac surface potentials on the defined cardiac surface geometry. The objective function of the regularization model can be defined as:

$$\min_{u_t}\left\{\frac{1}{2}\|Au_t - b_t\|_2^2 + \lambda TV(u_t)\right\} \quad (5)$$

where $$TV(u_t) = \|\nabla\|_1 = \sum_{\theta \in Directions} \|D^\theta u_t\|_1, \quad (6)$$

$\lambda \in \mathbb{R}$ is a regularization parameter that controls a trade-off between the fidelity term and the regularization term $TV(u_t)$, and θ is the search direction.

Since $TV(u_t)$ is not differentiable, iterative techniques can be implemented to reduce the complexity of the minimization problem by solving the constrained minimization problem $$\min_{u_t, d_t^\theta}\left\{\frac{1}{2}\|Au_t - b_t\|_2^2 + \lambda \sum_\theta \|d_t^\theta\|_1\right\}, \text{ subject to } D^\theta u_t = d_t^\theta, \quad (7)$$

for which closed form solutions exist. For this purpose, using the alternating direction method of multipliers (ADMM), for example, an iterative computation can be defined as follows:

$$\begin{cases} d_\theta^\theta = \text{shrinkage}\left(\sum_\theta |D^\theta u_t| + \widehat{d_t^\theta}, \lambda/\rho\right) \\ u_t = \arg\min\left\{\frac{1}{2}\|Au_t - b_t\|_2^2 + \frac{\rho}{2}\sum_\theta \|D^\theta u_t - d_t^\theta + \widehat{d_t^\theta}\|_2^2\right\} \\ \widehat{d_t^\theta} \leftarrow \widehat{d_t^\theta} + \gamma\sum_\theta (D^\theta u_t - d_t^\theta) \end{cases} \quad (8)$$

where the component-wise shrinkage operator is defined as $$\text{shrinkage}(x, \kappa) = \max(0, x-\kappa) - \max(0, -x-\kappa) \quad (9)$$

and parameters $\rho > 0$ and $\gamma \in (0, (\sqrt{5}+1)/2)$. Computation 8 is a prediction-correction process. The purpose of the $\widehat{d_t^\theta}$ term is to minimize error in the correction term $d_t^\theta$ so that the prediction-correction process converges faster, and to correct the difference between computed and predicted derivatives. The extrapolation step of computation 8 above aids the convergence of the algorithm when $D^\theta u_t$ and $d_t^\theta$ differ by large magnitudes. The notation $D^\theta$ indicates that there are multiple D matrices, one for each search direction. The rows of each D matrix correspond to the target-reference pairs, and the number of non-zero entries of each row depends on the number of nearest neighbors considered. For a given search direction, all the target-reference pairs on the graph are accumulated in a single D matrix.

Figure 5:
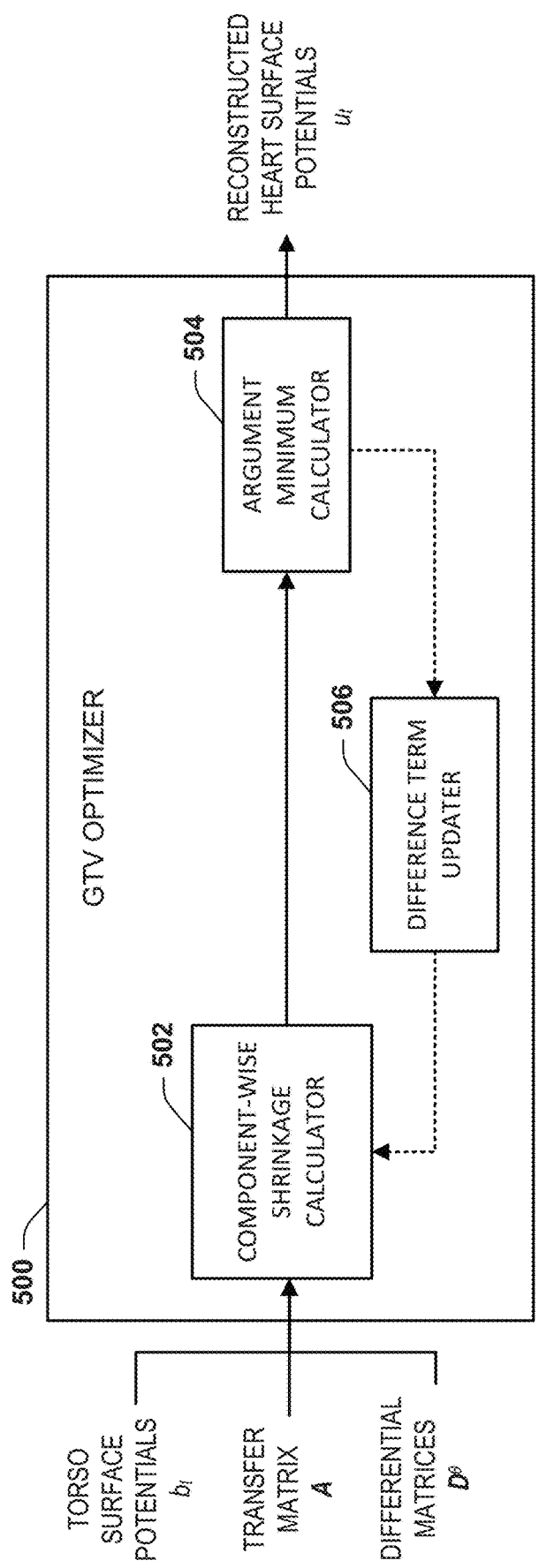
FIG. 5 is a block diagram of an example GTV optimizer.

FIG. 5 illustrates an example GTV optimizer 500 configured to perform the above ADMM computation to produce output reconstructed heart surface potentials $u_t$ based on input measured torso surface potentials $b_t$, transfer matrix A, and differential matrices $D^\theta$. GTV optimizer 500 can correspond to GTV optimizer 64 in FIG. 1 and can include component-wise shrinkage calculator 502, argument minimum calculator 504, and difference term updater 506. Each of these components can be configured to perform the three parts of the ADMM computation above, respectively, such that after a number of iterations the second term (following the plus sign) in the third part of the ADMM computation approaches zero. When this second term reaches less than a predetermined threshold value, the GTV optimization can be terminated and the output of the argument minimum calculator 504 can be output as the finally computed reconstructed heart surface potentials $u_t$. Another way of saying this is that the GTV optimizer 500 can complete the regularization computation and provide its reconstructed heart surface potentials output by terminating its 502-504-506 loop when the difference update term $\widehat{d_t^\theta}$ assigned in the third part of the ADMM computation changes between two successive iterations by less than a predetermined change threshold value.

Figure 6:
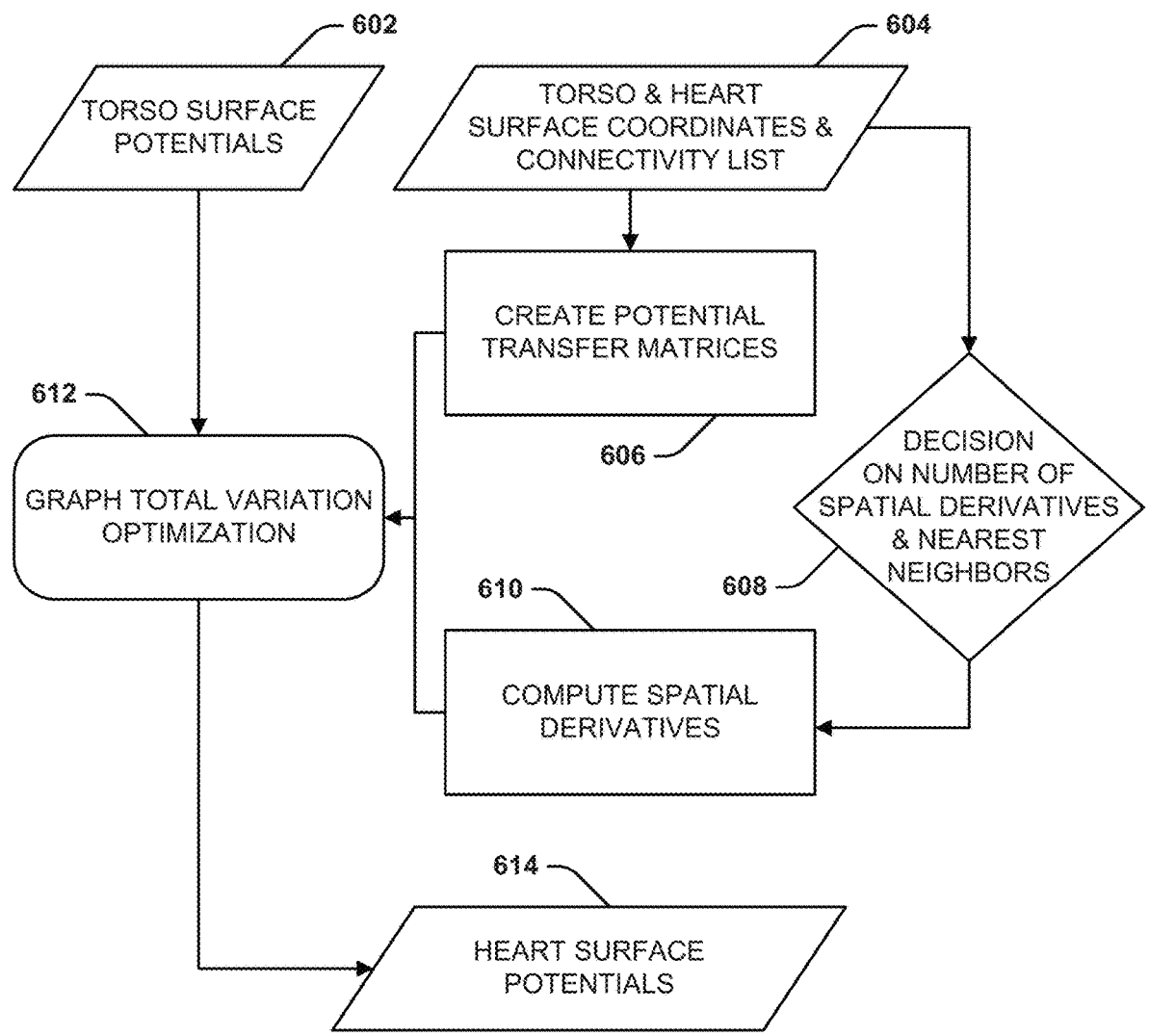
FIG. 6 is a flow chart of an example method of heart surface potential reconstruction using GTV regularization.

An example of the functioning of reconstruction engine 52 in FIG. 1 can is demonstrated in the flow chart of FIG. 6 and the following description. In this example, the inputs include electrode signals 602 measured on the torso surface as well as the geometry data 604, such as including the coordinates (vertices) and connectivity list (edges) of nodes on the torso where electrical signal measurements are made and the cardiac envelope (e.g., a heart surface). Using the geometry of the torso and cardiac envelope, transfer matrix A can be computed 306. As discussed previously, this matrix A tends to be ill-conditioned due to the nature of the sampled points. Thus, computing inverse matrix $A^{-1}$ without regularization will yield unsatisfactory results, and this is not performed in the method. The ill-posed effect of the transfer matrix can be reduced by increasing the density of the sampled points on the measurement surfaces.

The three-dimensional structures of the surfaces can be leveraged to improve upon the inverse by adding some contributing factor of the neighboring vertices to the reconstruction of the surface potential at a particular vertex. This can be done using the spatial derivatives on the surface. However, the vertices are generally not evenly distributed across the surfaces. Given the number Θ of directions to be explored with respect to each target node, e.g., eight directions, the neighboring vertices corresponding to a set of reference nodes, can be identified 608 in the $\Theta$ directions from a particular target node. An assumption can be made that, due to the nature of the geometry, the neighboring nodes one layer away from the target node define a sufficient sample of neighboring nodes that have a significant contributing effect for each given target node. Thus, in this example, for each search direction $\theta$ (up to $\Theta$), the derivative $D^\theta$ can be computed 610 and each entry can be normalized by either the geodesic distance or the Euclidean distance between the vertices (i.e., between the target node and the considered first-layer neighbor reference node). If the vertices really are evenly distributed across the surface, the normalization will be redundant as the neighboring nodes in each layer will have the same weights. The weights of each layer are determined using the 2D anisotropic spatial derivative which has a weighting factor of 1 at the location of the vertex in question (i.e., the target node), and a weight of $-1$ for vertices lying a layer away (i.e., reference nodes).

Graph total variation optimization 612 uses the computed transfer matrix A and differential operator matrices $D^\theta$. To reduce the effect of the ill-posedness of the transfer matrix in computing the inverse solution, the graph total variation optimization 612 implements GTV regularization that uses the spatial derivatives computed on the graph to reduce the condition number of the inverse operator to get a solution which has the desired properties on the heart surface. The condition number of the inverse operator is more reasonable in comparison to the naïve operator, and includes the information about sharp changes in the neighboring vertices. Graph total variation regularization enables solutions to be obtained where the regions of sharp changes are not smoothed out. This is the contributing effect of the spatial derivatives. After the iterations of the optimization 612 reach a sufficiently converged solution, the heart surface potentials 614 at a given time are output as a solution to the system. Accordingly, the GTV-based systems and methods described herein enforce the spatial smoothness of reconstructed signals in a different manner than presently used regularization schemes, such that large spatial signal changes are permitted while still reducing small changes. This allows the reconstruction to retain sharp details if the details are significant enough, as is particularly the case with R waves.

GTV-based methods and systems have diagnostic and therapeutic applications. For example, the systems and methods disclosed herein can be used as part of a diagnostic and/or treatment workflow to facilitate the identification and locating of fibrillation mechanisms based on electrical activity acquired for the patient. In some examples, the patient electrical activity can include non-invasive body surface measurements of body surface electrical activity. Additionally or alternatively, the patient electrical activity can include invasive measurements of heart electrical activity, including epicardial measurements and/or endocardial measurements. For example, a vest with a plurality of embedded electrodes can be placed on the torso to record the electrophysiological measurements from a plurality of nodes spaced over the torso. In some examples, the vest electrodes may cover only part of the torso region. In some examples, the vest can have 252 electrodes in contact with the torso surface to measure electrophysiological signals at selected locations.

The reconstructed electrical potentials can be computed across the cardiac surface as described above, and reconstructed potentials or information derived from the reconstructed potentials can be displayed as one or more generated graphical maps that can be presented on a display. For example, the graphical map can be an activation map or other map representing arrhythmogenic activity. This can be for a selected set of the signals distributed across the cardiac surface or for the entire three-dimensional cardiac surface and for one or more time intervals of interest, which can be selected in response to a user input. Examples of the types of output visualizations and maps that can be generated may be found in U.S. Pat. No. 9,427,169 and/or U.S. patent application publication No. 2014/0200822. The output can also include a graphical map illustrating body surface measurement channels from which certain events were detected. The output can also include a graphical representation of a region of the cardiac surface showing the estimated or determined location of origin of an event or activity designated for display.

Figure 7:
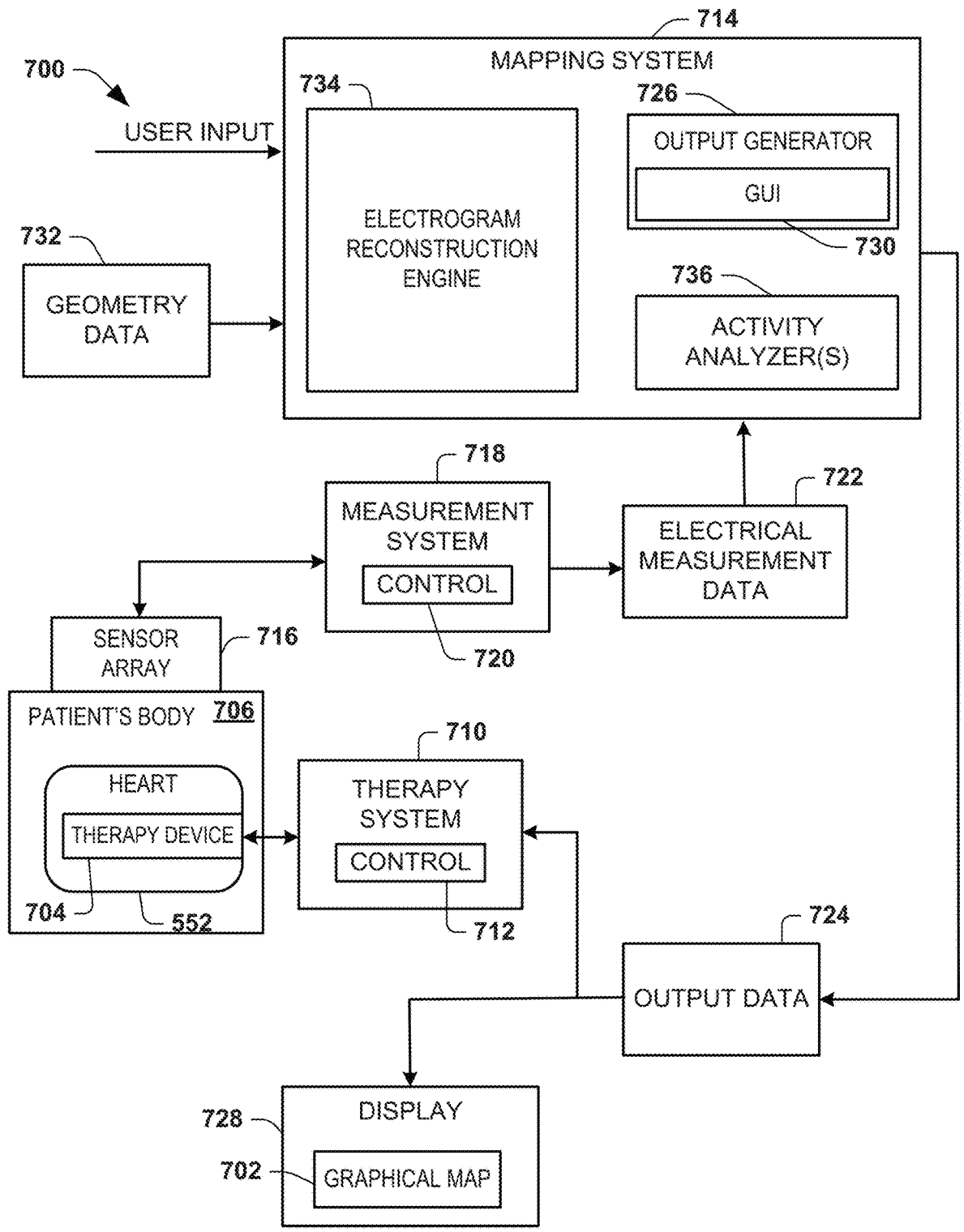
FIG. 7 is a block diagram of an example analysis and/or therapy system using GTV regularization in an electrogram reconstruction engine.

A user interface can be employed to set parameters for the graphical map(s) and to otherwise interact with and select portions of the electrophysiological data or reconstructed data in response to user input. FIG. 7 depicts an example of a system 700 that can be utilized for generating an output to process body surface signals as reconstructed cardiac surface potentials and/or to characterize arrhythmogenic activity of a patient. In some examples, the system 700 can generate a graphical map (e.g., a body surface map or a map on a heart model) 702 and/or display processed electrical signals. The system can also provide information in other formats to provide guidance to the user indicative of one or more of computed signal characteristics as well as information derived from such computed signal characteristics.

As disclosed herein, the system 700 has applications throughout various phases of patient care. As an example, the system can be used as part of a patient screening process (e.g., as part of a diagnostic and/or treatment planning procedure) or to perform post-treatment evaluation. Additionally, the system 700 can be utilized as part of a treatment procedure, such as to determine parameters for delivering a therapy to the patient (e.g., delivery location, amount and type of therapy). For example, a catheter, having one or more therapy delivery devices 704 affixed thereto can be inserted into the body 706 as to contact the patient's heart 708, endocardially or epicardially. Various types and configurations of therapy delivery devices 704 that can be utilized, which can vary depending on the type of treatment and the procedure. For instance, therapy device 704 can be configured to deliver electrical therapy, chemical therapy, sound wave therapy, thermal therapy or any combination thereof.

By way of further example, the therapy delivery device 704 can include one or more electrodes located at a tip of an ablation catheter configured to generate heat for ablating tissue in response to electrical signals (e.g., radiofrequency energy) supplied by a therapy system 710. In other examples, the therapy delivery device 704 can be configured to deliver cooling to perform ablation (e.g., cryogenic ablation), to deliver chemicals (e.g., drugs), ultrasound ablation, high-frequency radio frequency ablation, or a combination thereof. In still other examples, the therapy delivery device 704 can include one or more electrodes located at a tip of a pacing catheter to deliver electrical stimulation, such as for pacing the heart, in response to electrical signals (e.g., pacing current pulses) supplied by a therapy system 710. Other types of therapy can also be delivered via the therapy system 710 and the invasive therapy delivery device 704 that is positioned within the body 706.

As a further example, the therapy system 710 can be located external to the patient's body 706 and be configured to control therapy that is being delivered by the device 704.

For instance, the therapy system 710 includes controls (e.g., hardware and/or software) 712 that can communicate (e.g., supply) electrical signals via a conductive link electrically connected between the delivery device (e.g., one or more electrodes) 704 and the therapy system 710. The control system 712 can control parameters of the signals supplied to the device 704 (e.g., current, voltage, repetition rate, trigger delay, sensing trigger amplitude) for delivering therapy (e.g., ablation or stimulation) via the electrode(s) 706 to one or more location of the heart 708. The control circuitry 712 can set the therapy parameters and apply stimulation based on automatic, manual (e.g., user input) or a combination of automatic and manual (e.g., semiautomatic controls). One or more sensors (not shown) can also communicate sensor information back to the therapy system 710. The position of the device 704 relative to the heart 708 can be determined and tracked intraoperatively via an imaging modality (e.g., fluoroscopy, X ray), a mapping system 714, direct vision or the like. The location of the device 704 and the therapy parameters thus can be combined to determine corresponding therapy delivery parameter.

Before, during and/or after providing a therapy via the therapy system 710, another system or subsystem can be utilized to acquire electrophysiology information for the patient. In the example of FIG. 7, a sensor array 716 includes one or more body surface electrodes that can be utilized for measuring patient electrical activity. As one example, the sensor array 716 can correspond to a high-density arrangement of body surface sensors (e.g., greater than approximately one hundred electrodes, e.g., greater than approximately two hundred electrodes, e.g., two hundred fifty-two electrodes) that are distributed over a portion of the patient's torso (e.g., thorax) for measuring electrical activity associated with the patient's heart (e.g., as part of an electrocardiographic mapping procedure). Examples of a high-density body surface non-invasive apparatus that can be used as the sensor array 716 are shown and described in U.S. Pat. No. 9,655,561 and international publication No. WO 2010/054352. Other arrangements and numbers of sensing electrodes can be used as the sensor array 716. For example, the array can be a reduced set of electrodes, which does not cover the patient's entire torso and is designed for measuring electrical activity for a particular purpose (e.g., an array of electrodes specially designed for analyzing atrial fibrillation and/or ventricular fibrillation) and/or for monitoring a predetermined spatial region of the heart. In other examples, an array having a traditional or modified 12-lead ECG or a single electrode can be implemented as the sensor array 716 to provide body surface electrical signals.

In some examples, one or more sensors may also be located on the device 704 that is inserted into the patient's body. Such sensors can be utilized separately or in conjunction with the non-invasive sensor array 716 for mapping electrical activity for an endocardial surface, such as the wall of a heart chamber, as well as for a cardiac surface. Additionally, such electrode can also be utilized to help localize the device 704 within the heart 708, which can be registered into an image or map that is generated by the system 700. Alternatively, such localization can be implemented in the absence of emitting a signal from an electrode within or on the heart 708.

In each of such example approaches for acquiring patient electrical information, including invasively, non-invasively, or a combination of invasive and non-invasive sensing, the sensor array(s) 716 provide the sensed electrical information to a corresponding measurement system 718. The measurement system 718 can include appropriate controls 720 for providing electrical measurement data 722 that describes electrical activity (e.g., ECG signals) detected by the sensors in the sensor array 716. For example, signal processing circuitry of the measurement system 718 can convert the signal(s) to corresponding digital information. The measurement system 718 can further process the digital information corresponding to one or more electrophysiological signals from sensor array 716 and remove non-arrhythmogenic characteristics from each such signal and to provide preprocessed data that is stored in memory as the electrical measurement data 722. Electrical measurement data 722 can correspond, for example, to electrical data 58 in FIG. 1.

The control 720 can also be configured to control the data acquisition process for measuring electrical activity and providing the measurement data 722 (e.g., at a predefined sample rate). In some examples, the control 720 can control acquisition of measurement data 722 separately from operation of the therapy system 710 (if implemented), such as in response to a user input. In other examples, the measurement data 722 can be acquired concurrently with and in synchronization with delivering therapy by the therapy system, such as to detect electrical activity of the heart 708 that occurs in response to applying a given therapy (e.g., according to therapy parameters). For instance, appropriate time stamps can be utilized for indexing the temporal relationship between the respective measurement data 722 and therapy parameters use to deliver therapy as to facilitate the evaluation and analysis thereof.

The mapping system 714 can be programmed to combine the measurement data 722 corresponding to sensed body surface electrical activity of the heart 708 to provide corresponding output data 724. The output data 724 can be represent or characterize detected ECG signals on the body surface and/or within the heart. The output data can also represent information derived from the measured signals, such as reconstructed electrogram signals, as disclosed herein.

The mapping system 714 can include an output generator 726 to provide the output data 724 to visualize on a display 728 one or more intervals of ECG signals based on the electrical measurement data acquired for the patient over one or more time intervals (e.g., before, after or during an EP procedure or treatment procedure). In an example where the sensor array 716 includes a plurality of electrodes, the output data 724 can include a selected set of channels for ECG signals measured via sensors 716 on the patient's body surface. Parameters can be set to identify a subset of signals meeting one or more user configurable parameters (e.g., via GUI 730). The output generator 726 thus can generate the output data 724 to display a graphical representation of time-domain plots, frequency-domain plots, channels as arranged on the torso, or regions mapped to the cardiac surface.

In some examples, computed data can be mapped to a geometric surface of a heart model. As disclosed herein, the maps can be computed based on electrical data 722 that is acquired non-invasively via one or more electrodes in the sensor array 716 distributed on the surface of the patient's body 706.

Since the measurement system 718 can measure electrical activity of a predetermined region or the entire heart concurrently (e.g., where the sensor array 716 including a plurality of electrodes covers the entire thorax of the patient's body 706), the resulting output data (e.g., ECG signals and/or electrocardiographic maps) 724 thus can also represent concurrent data for the predetermined region or the entire heart in a temporally and spatially consistent manner.

The time interval for which the output data/maps are computed can be selected based on user input. Additionally or alternatively, the selected intervals can be synchronized with the application of therapy by the therapy system 710. As disclosed herein, the indication of the presence or absence of stable arrhythmogenic activity can be computed from the body surface electrical signal(s) in the absence of performing electrogram reconstruction based on patient geometry.

In other examples, where additional information may be available and geometry data 732 can be obtained, the system may include electrogram reconstruction engine 734 programmed to compute an inverse solution and provide corresponding reconstructed electrograms based on the process signals and the geometry data 732. Electrogram reconstruction engine 734 can correspond to reconstruction engine 52 in FIG. 1, and thus can operate based on the graph total variation (GTV) based reconstruction methods and systems described herein. For example, the reconstruction engine 734 implements instructions, which are executable by one or more processors, to perform functions corresponding to transfer matrix generator, spatial derivative operator calculator and GTV optimization functions, as disclosed herein.

The geometry data 732 can correspond to a mathematical model, such as can be a generic model or a model that has been constructed based on image data obtained for the patient (e.g., via an imaging modality, such as CT, MRI, bi-plane X ray or the like) and can provide spatial coordinates for the patient's heart 708 and electrodes on the sensor array 716. The reconstructed electrograms thus can correspond to electrocardiographic activity across a cardiac envelope, and can include static (three-dimensional at a given instant in time) and/or be dynamic (e.g., four-dimensional map that varies over time). Examples of inverse algorithms that can be utilized in the reconstruction engine 734 include those disclosed in U.S. Pat. Nos. 7,983,743 and 6,772,004. The electrogram reconstruction engine 734 thus can reconstruct the body surface electrical activity measured via the sensor array 716 onto a multitude of locations on a cardiac envelope (e.g., greater than 1,000 locations, such as about 2,000 locations or more). In other examples, the mapping system 714 can compute electrical activity over a sub-region of the heart based on electrical activity measured invasively, such as via a basket catheter or other form of measurement probe (e.g., on or attached to device 704).

Mapping system 714 can further include one or more other cardiac electrical activity analyzer(s) 736, for example, an arrhythmia driver analyzer, to analyze reconstructed electrograms and thereby determine the causes or sources of harmful or undesirable cardiac electrical activity. Based on this analysis, which is improved by the more faithful reconstructed signals generated by the electrogram reconstruction engine 734, enhanced diagnostics and therapies can be provided to a patient.

Parameters associated with the graphical representation, corresponding to an output visualization of the computed map, such as including selecting a time interval, a type of information that is to be presented in the visualization and the like can be selected in response to a user input via a corresponding visualization GUI 730.

Additionally, the output data 724 can be utilized by the therapy system 710, if included in the system 700. The control that is implemented can be fully automated control, semi-automated control (partially automated and responsive to a user input) or manual control based on the output data 724. In some examples, the control 712 of the therapy system can utilize the output data to control one or more therapy parameters. As an example, the control 712 can control delivery of ablation therapy to a site of the heart (e.g., epicardial or endocardial wall) based on GTV reconstruction data disclosed herein that has been determined by the reconstruction engine 734. For instance, the delivery of therapy can be terminated automatically in response to detecting the absence of symptoms or arrhythmogenic activity after a time period, or the absence of stable driver activity after a time period. In other examples, an individual user can view the map 702 generated in the display 728 to manually control the therapy system 710 based on information that is visualized. Other types of therapy and devices can also be controlled based on the output data 724. The output data 724, as analyzed and/or displayed, can also provide indication of the progress or success of the therapy, so as to assure user and/or patient that the therapy has provided the intended effect and/or achieved the intended therapeutic goal.

In view of the above, cardiac diagnostics and therapeutics are improved by the systems and methods disclosed herein. In the below description of experimental evaluations of the performance of the GTV-based reconstruction methods described herein, $u$ and $\hat{u}$ represent the observed ground truth signal and the reconstructed signal, respectively, and the following qualitative performance measures can be used.

Root mean squared error (RMSE) measures the standard deviation of the difference between the predicted and observed signal. It is defined by $$MSE(u, \hat{u}) = \frac{1}{n}\sum_{i=1}^{n}(\hat{u}_i - u_i)^2 \qquad (10)$$

$$RMSE(u, \hat{u}) = \sqrt{MSE(u, \hat{u})} \qquad (11)$$

The lower the value of the RMSE estimate, the better the reconstruction.

Peak signal-to-noise ratio (PSNR) measures the ratio of the strength of a signal and that of the corrupting noise that affects the fidelity of the signal.

$$PSNR(u, \hat{u}) = 10 \cdot \log_{10}\left(\frac{MAX_u^2}{MSE(u, \hat{u})}\right) \qquad (12)$$

Higher PSNR estimates imply a high quality reconstruction.

Cross correlation (CC) measures the similarity between the predicted and the observed signal and can be expressed as $$CC(u, \hat{u}) = \frac{\text{cov}(u, \hat{u})}{\sigma_u \sigma_{\hat{u}}} \qquad (13)$$

Total reconstruction error (TRE) measures the overall reconstruction accuracy is given by $$TRE(u, \hat{u}) = \frac{\|\hat{u} - u\|_2}{\|u\|_2} \qquad (14)$$

Estimation of the value of the regularization parameter $\lambda$ can be made with consideration of the following methods.

L-curve: The L-curve method provides a measure for λ by estimating the value for which the log-log plot of the fidelity ($\|Au_t-b_t\|_2$) and regularity term ($\|\nabla u_t\|_1$) kinks.

General-cross validation (GCV): This measure assumes that the measured data ($b_t$) is affected by normally distributed noise. The optimal value of λ is that which minimizes the function $$G(\lambda) = \frac{\|(I - AA_\lambda^\#)b_t\|_2}{\text{trace}(I - AA_\lambda^\#)} \quad (15)$$

where $A_\lambda^\#$ denotes the matrix that maps the right-hand side $b_t$ onto the regularized solution $u_r(\lambda)$.

Minimal Product: Similar to the L-curve method, this technique can be adapted for both continuous and discrete regularization to find the value that minimizes $$P(\lambda)=\|\nabla u_r(\lambda)\|_1 \cdot \|Au_r(\lambda)-b_t\|_2. \quad (16)$$

The parameter ρ controls the convergence speed of the algorithm and is set to cλ for a suitably chosen value of c ∈ ℝ. Higher orders of smoothness can be achieved by using fractional-order derivatives. However, in the experimental evaluations described below, the traditional TV case using the first-order spatial derivative is considered. The parameter γ is fixed as 1.

The GTV-based methods have been compared with their state-of-the-art Tikhonov-based counterparts in reconstructing ECG signals within the method of fundamental solutions (MFS) and the boundary element method (BEM) frameworks. The performance of the GTV methods described herein have been evaluated using the first-order spatial derivative D defined in equation 3, above. The results show the reconstructed potentials at selected source localizations, activation maps and a composite of the recovered signals. Quantitative estimates are summarized in the subsequent tables.

The model was first tested in the case of denoising for uniform and nonuniform meshes. The below table compares Tikh, TV, and GTV regularized solutions on a uniform rectangular grid with 30% Gaussian noise.

|  | PSNR | RMSE | CC | TRE |
|---|---|---|---|---|
| Tikh | 15.9918 | 0.1586 | 0.9619 | 0.2243 |
| TV | 12.4537 | 0.23841 | 0.9447 | 0.3372 |
| GTV | 22.7293 | 0.0730 | 0.9954 | 0.1033 |
| Reference | ∞ | 0 | 1 | 0 |

The below table compares Tikh, TV, and GTV regularized solutions on a non-uniform triangular mesh with 25% Gaussian noise.

|  | PSNR | RMSE | CC | TRE |
|---|---|---|---|---|
| Tikh | 11.6613 | 0.2612 | 0.8695 | 0.3023 |
| TV | 14.1632 | 0.1958 | 0.8954 | 0.2267 |
| GTV | 14.2345 | 0.1942 | 0.9850 | 0.2248 |
| Reference | ∞ | 0 | 1 | 0 |

The below table compares Tikh, TV, and GTV regularized solutions on a non-uniform three-dimensional triangular mesh with 35% Gaussian noise.

|  | PSNR | RMSE | CC | TRE |
|---|---|---|---|---|
| Tikh | 09.2781 | 0.3436 | 0.7067 | 0.9027 |
| TV | 12.5822 | 0.2349 | 0.7663 | 0.6170 |
| GTV | 21.6668 | 0.0825 | 0.9938 | 0.2168 |
| Reference | ∞ | 0 | 1 | 0 |

Figure 8:
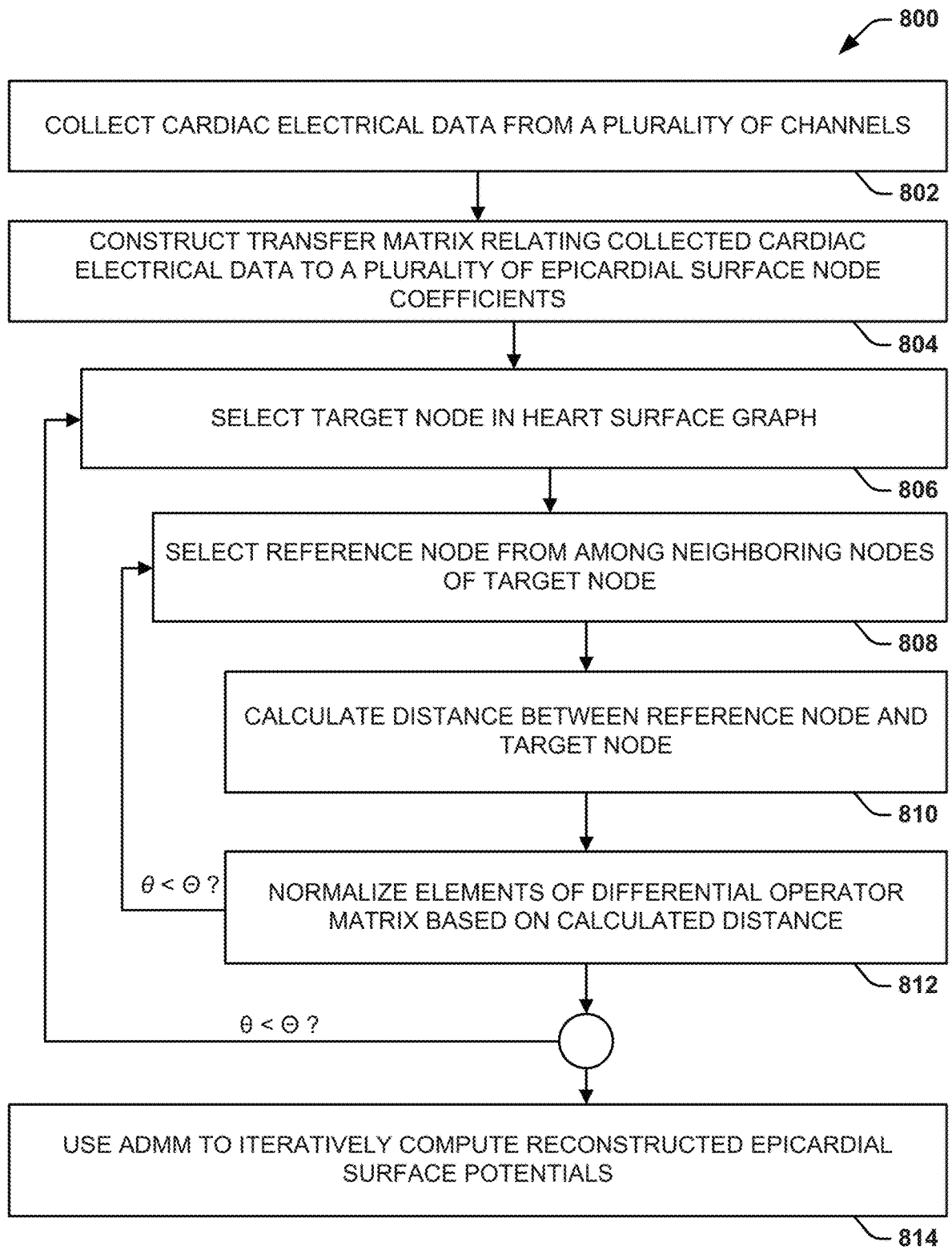
FIG. 8 is a flow chart depicting a method of GTV for ECG potential reconstruction.

FIG. 8 is a flow chart depicting an example method 800 of GTV-based electrogram reconstruction. The method 800 can include collecting 802 cardiac electrical data from a plurality of channels, e.g., as may be obtained from an array of electrodes on the body surface (e.g., thorax) of a patient, e.g., in excess of one hundred channels, e.g., in excess of two hundred channels, e.g., two hundred fifty-two channels. Based on geometry data indicative of geometrical properties of body and cardiac surfaces, there can be constructed 804 a transfer matrix that relates the collected cardiac electrical data to a plurality of cardiac surface node coefficients. For each of a plurality of target nodes 806 among cardiac surface nodes in the geometry data, up to a predetermined maximum number of reference nodes can be selected 808 among the cardiac surface nodes neighboring the target node, and the distances between the target node and each reference node can be calculated 810. Based on the calculated distances, the elements of a set of differential operator matrices can be normalized 812.

Additional reference nodes can be selected 808 up to a maximum number Θ, e.g., five, six, seven, or eight, and the process can repeat for additional target nodes 806 until it has been done for all target nodes, or for a selected subset of target nodes, or for a sufficient number of target nodes such that some density criterion is met. The method 800 can then iteratively compute 814, by an alternating direction method of multipliers (ADMM), reconstructed cardiac surface potentials based on the collected cardiac electrical data, the transfer matrix, and the differential operator matrices. A graphical output indicative of the reconstructed electrograms or analysis based on the reconstructed electrograms can be provided, e.g., via a visual display. A displayed graphical map can be used to guide a therapy, e.g., an ablation or a drug delivery, and/or can be used to automatically control therapy delivery, as described herein.

In view of the foregoing structural and functional description, those skilled in the art will appreciate that portions of the invention may be embodied as a method, data processing system, or computer program product. Accordingly, these portions of the present invention may take the form of an entirely hardware embodiment, an entirely software embodiment, or an embodiment combining software and hardware. Furthermore, portions of the invention may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments of the invention have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

What have been described above are examples. It is, of course, not possible to describe every conceivable combination of components or methods, but one of ordinary skill in the art will recognize that many further combinations and permutations are possible. Accordingly, the invention is intended to embrace all such alterations, modifications, and variations that fall within the scope of this application, including the appended claims. Where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, the term "including" means including but not limited to. The term "based on" means based at least in part on."

The invention claimed is:

1. A graph total variation (GTV) based electrogram reconstruction method comprising:
   based on geometry data indicative of geometrical properties of body and cardiac surfaces, constructing a transfer matrix that relates acquired cardiac electrical data, representing electrophysiological signals collected via a plurality of body surface measurement channels, to a plurality of cardiac surface node coefficients;
   for each of a plurality of target nodes among cardiac surface nodes on a cardiac surface mesh represented in the geometry data,
      selecting at least one reference node on the cardiac surface mesh among the cardiac surface nodes neighboring the target node,
      calculating distances along the cardiac surface between the target node and each selected reference node, and normalizing elements of a set of differential operator matrices based on the calculated distances to provide normalized differential operator matrices; and
   iteratively computing reconstructed cardiac surface potentials based on the collected cardiac electrical data, the transfer matrix, and the normalized differential operator matrices,
   wherein the GTV-based electrogram reconstruction method performs the selecting, the calculating, and the normalizing using nodes only from among the cardiac surface nodes on the cardiac surface mesh.

2. The method of claim 1, further comprising outputting a graphical map of the reconstructed cardiac surface potentials visualized on a three-dimensional model of the heart surface to a display.

3. The method of claim 1, further comprising analyzing the reconstructed cardiac surface potentials to provide an indication of the progress or success of a cardiac therapy.

4. The method of claim 1, wherein the selecting the at least one reference node comprises selecting up to a predetermined maximum number of reference nodes selected among the cardiac surface nodes neighboring the target node, and wherein the predetermined number is at least three.

5. The method of claim 1, wherein only first-layer neighbors of the target node are selected as reference nodes, or wherein all neighbors within a predefined target-reference distance are selected as reference nodes.

6. The method of claim 1, wherein the iteratively computing uses an alternating direction method of multipliers (ADMM) that comprises, in each iteration thereof, a component-wise shrinkage calculation, an argument minimum calculation, and an updating of a difference term.

7. The method of claim 6, wherein ADMM iterative computing is configured to terminate when the difference term changes between two successive ADMM iterations by less than a threshold value.

8. The method of claim 1, wherein the selecting the at least one reference node comprises selecting up to a predetermined maximum number of reference nodes among the cardiac surf ace nodes neighboring the target node by choosing a nearest node to the target node distributed evenly around the target node.

9. The method of claim 8, wherein the number of differential operator matrices is the predetermined maximum number.

10. The method of claim 1, wherein, prior to the normalizing, each differential operator matrix represents a weighting factor of 1 at the location of the target node and a weight of −1 at the locations of first-layer reference nodes.

11. A system comprising:
   non-transitory memory configured to store electrical data representing a plurality of electrocardiogram signals, geometry data and machine-readable instructions; and
   a processor configured to access the non-transitory memory and execute the machine-readable instructions, the instructions comprising:
      a transfer matrix generator programmed to construct a transfer matrix that relates collected electrophysiological data from a plurality of body surface measurement channels to a plurality of cardiac surface node coefficients, based on geometry data representing spatial geometry of the body surface and spatial geometry of a cardiac surface in a three-dimensional coordinate system;
      a spatial derivative operator calculator programmed to calculate a set of spatial derivative operators based on the cardiac surface geometry data; and
      a graph total variation (GTV) optimizer programmed to iteratively compute, using an alternating direction method of multipliers (ADMM), reconstructed cardiac surface potentials based on the collected electrophysiological data, the transfer matrix, and the spatial derivative operators,
      wherein the transfer matrix generator, the spatial derivative operator calculator, and the GTV optimizer are programmed to operate only on cardiac surface nodes in the cardiac surface geometry data.

12. The system of claim 11, wherein the spatial derivative operator calculator is programmed to calculate a predetermined maximum number of spatial derivative operators for each target node in the portion of the geometry data indicative of the geometrical properties of the cardiac surface, the spatial derivative operators corresponding to reference nodes selected among the cardiac surface nodes neighboring the target node.

13. The system of claim 12, wherein only first-layer neighbors of the target node are selected as reference nodes, or wherein all neighbors within a predefined target-reference distance are selected as reference nodes.

14. The system of claim 11, wherein the GTV optimizer comprises a component-wise shrinkage calculator, an argument minimum calculator, and difference term updater, arranged in a loop.

15. The system of claim 14, wherein the loop is configured to terminate when the difference term changes between two successive ADMM iterations by less than a threshold value.

16. A system comprising:
- an array of electrophysiological sensors configured to be placed on a body surface of a patient and thereby to produce electrical measurement data corresponding to electrical potentials measured from the body surface;
- a mapping system comprising an electrogram reconstruction engine configured to reconstruct electrograms on a cardiac surface based on the electrical measurement data and on geometry data, the geometry data representing spatial geometry of the body surface and the cardiac surface in a three-dimensional coordinate system, the electrogram reconstruction engine configured to perform a graph total variation (GTV) regularization that normalizes the elements of a set of differential operator matrices based on calculated distances between target and neighboring reference nodes in the cardiac surface geometry data and iteratively computes, by an alternating direction method of multipliers (ADMM), reconstructed cardiac surface potentials based on the electrical measurement data and the differential operator matrices; and
- a display configured to visualize a graphical map that is based on the reconstructed electrograms,
- wherein the GTV regularization is configured to operate on nodes only on the cardiac surface in the cardiac surface geometry data.

17. The system of claim 16, further comprising a cardiac therapy system controlled by output data that is based on the reconstructed electrograms.

18. The system of claim 17, wherein the display provides an indication of progress or success of a therapy provided by the cardiac therapy system.

19. The system of claim 16, wherein the electrogram reconstruction engine comprises a transfer matrix generator configured to construct a transfer matrix that relates the electrical measurement data to a plurality of cardiac surface node coefficients, based on geometry data indicative of geometrical properties of body and cardiac surfaces.

20. The system of claim 16, wherein the number of differential operator matrices in the set is limited to a predetermined maximum number of at least three.

* * * * *